US012758349B2

(12) United States Patent
Spang

(10) Patent No.: US 12,758,349 B2
(45) Date of Patent: *Oct. 13, 2026

(54) FRAME

(71) Applicant: Mosaic Surgical Limited, High Wycombe (GB)

(72) Inventor: Angela Spang, High Wycombe (GB)

(73) Assignee: Mosaic Surgical Limited, High Wycombe (GB)

(*) Notice: Subject to any disclaimer, the term of this patent is extended or adjusted under 35 U.S.C. 154(b) by 0 days.

This patent is subject to a terminal disclaimer.

(21) Appl. No.: 18/968,514

(22) Filed: Dec. 4, 2024

(65) Prior Publication Data

US 2026/0000476 A1 Jan. 1, 2026

(30) Foreign Application Priority Data

Jul. 1, 2024 (GB) ..................................... 2409502
Nov. 21, 2024 (GB) ..................................... 2417126

(51) Int. Cl.

| | |
|---|---|
| ***A61B 90/00*** | (2016.01) |
| ***A61B 17/02*** | (2006.01) |
| ***A61G 13/12*** | (2006.01) |
| *A61B 90/14* | (2016.01) |

(52) U.S. Cl.

CPC .......... *A61B 90/08* (2016.02); *A61B 17/0293* (2013.01); *A61G 13/124* (2013.01); *A61B 2017/0287* (2013.01); *A61B 90/14* (2016.02)

(58) Field of Classification Search

CPC .... A45D 29/22; A61B 17/0293; A61B 17/02; A61B 2017/0212; A61B 2017/0287; A61B 90/08; A42B 3/08; A61G 13/0045; A61G 13/124

See application file for complete search history.

(56) References Cited

U.S. PATENT DOCUMENTS 2,291,125 A 7/1942 Wilkinson
2,612,891 A 10/1952 Smith
3,746,332 A * 7/1973 Hakstian .............. A61G 13/124 5/647
3,762,401 A 10/1973 Tupper (Continued)

FOREIGN PATENT DOCUMENTS

CN 207506643 6/2018
CN 214434725 10/2021

(Continued)

OTHER PUBLICATIONS

June Medical, Introduction to HandMe Galaxy II Retractor for hand surgery, Published Sep. 25, 2024, YouTube https://youtu.be/4c_4FVeoEcY?si=Ag3aDYMOeu6y1Js8 (Year: 2024).*

(Continued)

*Primary Examiner* — Jacqueline T Johanas
(74) *Attorney, Agent, or Firm* — ICE MILLER LLP

(57) ABSTRACT

The present invention provides a frame for supporting digits which may be used during surgery to elevate digits during an operation. The frame comprises a plate with two wings which define a plane and a space therebetween, an engaging feature on each wing for removable engagement with retaining ties, and an elevated support surface between the wings to support digits. The frame provides a secure platform for supporting digits during hand surgery.

20 Claims, 11 Drawing Sheets

(56) References Cited

U.S. PATENT DOCUMENTS

| | | | | |
|---|---|---|---|---|
| 4,082,257 | A * | 4/1978 | Strickland | A61G 13/0045 5/606 |
| 4,434,791 | A * | 3/1984 | Darnell | A61B 17/0293 600/233 |
| 4,549,537 | A * | 10/1985 | Ender | A61F 5/05866 602/21 |
| 4,662,364 | A * | 5/1987 | Viegas | A61F 5/05866 602/21 |
| 4,798,195 | A | 1/1989 | Seare, Jr. | |
| 4,807,864 | A * | 2/1989 | Young | A61G 13/0045 5/617 |
| 4,915,331 | A * | 4/1990 | Becker | A45D 29/22 132/73 |
| 5,121,743 | A * | 6/1992 | Bishop | A61F 5/05866 D24/190 |
| 5,140,998 | A | 8/1992 | Vickers | |
| 5,357,654 | A * | 10/1994 | Hsing-Chi | A63B 33/002 2/418 |
| 5,372,145 | A * | 12/1994 | Berger | A61G 13/0045 602/20 |
| 5,547,463 | A * | 8/1996 | Hinchliffe | A61B 90/00 600/102 |
| 5,730,152 | A * | 3/1998 | Esser | A61G 13/0045 128/845 |
| 5,759,165 | A * | 6/1998 | Malewicz | A61F 5/0125 602/21 |
| 5,771,901 | A * | 6/1998 | O'Brien | A61F 5/0118 128/878 |
| 5,919,151 | A * | 7/1999 | Gustafson | A61F 5/32 128/878 |
| 5,951,467 | A | 9/1999 | Picha et al. | |
| 5,983,406 | A * | 11/1999 | Meyerrose | B63C 11/12 2/452 |
| 6,077,221 | A | 6/2000 | Fowler, Jr. | |
| 6,090,043 | A | 7/2000 | Austin et al. | |
| 6,113,577 | A * | 9/2000 | Hakky | A61M 25/02 604/179 |
| 6,520,925 | B1 * | 2/2003 | Thibodo, Jr. | A61F 5/05875 128/880 |
| 6,662,744 | B2 * | 12/2003 | Wallhouse | A63C 11/00 40/607.13 |
| 6,824,511 | B1 * | 11/2004 | Bell | A61B 17/02 600/227 |
| 6,945,252 | B2 * | 9/2005 | Mengato | A61F 5/05866 128/880 |
| 7,491,186 | B2 * | 2/2009 | Zeide | A61F 5/0118 602/5 |
| 8,006,699 | B2 * | 8/2011 | Rozier | A61M 25/02 128/877 |
| 10,080,679 | B2 * | 9/2018 | Grunden | A61F 5/0118 |
| 10,363,198 | B2 * | 7/2019 | Salstein-Begley | A61H 39/04 |
| 11,963,912 | B2 * | 4/2024 | Lewold | A61G 13/124 |
| 12,433,809 | B2 * | 10/2025 | Grabow | A61G 13/0045 |
| 12,605,225 | B2 * | 4/2026 | Spang | A61B 17/02 |
| 2003/0004401 | A1 * | 1/2003 | Ball | A61B 17/0293 600/233 |
| 2005/0171405 | A1 | 8/2005 | Rowland et al. | |
| 2005/0215865 | A1 * | 9/2005 | LeVahn | A61B 17/0206 600/231 |
| 2006/0129077 | A1 * | 6/2006 | Parizot | A61F 5/028 602/61 |
| 2006/0137071 | A1 * | 6/2006 | Rampersad | A41D 13/0556 2/24 |
| 2006/0272979 | A1 | 12/2006 | Lubbers et al. | |
| 2007/0161866 | A1 * | 7/2007 | Fowler | A61B 17/0293 600/233 |
| 2007/0167893 | A1 * | 7/2007 | Frisbie | A61F 5/0113 602/12 |
| 2007/0238933 | A1 | 10/2007 | Alinson et al. | |
| 2007/0293730 | A1 * | 12/2007 | Rioux | A61B 17/0293 600/231 |
| 2008/0163876 | A1 * | 7/2008 | Phelan | A61F 5/0118 602/21 |
| 2008/0269564 | A1 | 10/2008 | Gelnett | |
| 2011/0168487 | A1 * | 7/2011 | Steck | A62B 35/0031 24/115 R |
| 2011/0295075 | A1 * | 12/2011 | Picha | A61B 17/0293 600/206 |
| 2015/0068534 | A1 | 3/2015 | Lubbers et al. | |
| 2015/0127099 | A1 * | 5/2015 | Brunnett | A61F 2/2448 623/2.36 |
| 2015/0320928 | A1 | 11/2015 | Allen | |
| 2017/0196749 | A1 * | 7/2017 | Hatch | A61G 13/124 |
| 2017/0303914 | A1 * | 10/2017 | Sengun | A61B 17/0469 |
| 2018/0055708 | A1 * | 3/2018 | Hatch | A61G 13/1235 |
| 2021/0145682 | A1 * | 5/2021 | Grabow | A61G 13/101 |
| 2022/0071795 | A1 * | 3/2022 | Seymour | A61G 13/1295 |
| 2022/0167963 | A1 * | 6/2022 | Hustedt | A61B 17/0401 |
| 2023/0255611 | A1 * | 8/2023 | Richards | A61B 1/32 600/206 |
| 2023/0353666 | A1 * | 11/2023 | Kim | H04M 1/0279 |
| 2025/0000503 | A1 * | 1/2025 | Diez | A61B 17/0293 |
| 2025/0057680 | A1 * | 2/2025 | MacArthur | A61F 5/0118 |

FOREIGN PATENT DOCUMENTS

| | | | | |
|---|---|---|---|---|
| CN | 216628742 | | 5/2022 | |
| CN | 219846832 | U | 10/2023 | |
| FR | 2968534 | | 6/2012 | |
| GB | 6362403 | | 5/2024 | |
| GB | 2635283 | A * | 5/2025 | A61B 90/14 |
| JP | 2002-531158 | A | 9/2002 | |
| JP | 2008-178705 | A | 8/2008 | |
| JP | 2019-111041 | A | 7/2019 | |

OTHER PUBLICATIONS

Combined Search and Examination Report issued in GB2409502.8, mailed on Oct. 30, 2024. (6 pages).

GB Search Report mailed in GB2504870.3, dated May 23, 2025.

GB Search Report mailed in GB2505244.0, dated May 23, 2025.

European extended search report issued in EP 25179927.6, dated Nov. 3, 2025.

GB Search Report mailed in GB409502.8, dated Mar. 6, 2025.

Japanese Office Action from Japanese Patent Application No. 2025-069647, mailed Jun. 2, 2026 and English translation. (6 pages).

* cited by examiner

FRAME

CROSS-REFERENCE TO RELATED APPLICATIONS

This application claims priority to and the benefit thereof from UK Patent Application No. GB2417126.6, filed on 21 Nov. 2024, and UK Patent Application No. GB2409502.8, filed on 1 Jul. 2024, titled "Frame," which are hereby incorporated by reference in their respective entireties.

FIELD OF THE INVENTION

The present invention provides a frame for supporting a digit during surgery, a securing device, a kit comprising a frame, a securing device, methods of preparing a hand for surgery and methods of surgery.

BACKGROUND OF THE INVENTION

During surgery it is sometimes necessary to hold back flaps of skin or other tissue to enable a surgeon to access underlying tissue.

There are several options for holding back tissue, including physical holding of tissue by an assistant, the use of clamps, sutures and frames. Often these solutions are used in combination. Frames for holding back tissue are supplied by June Medical Limited, of 9 York Way, High Wycombe, Buckinghamshire, England, HP12 3PY under the Galaxy II® brand. These products are sometimes referred to as retractor frames. In these products a frame surrounds the tissue which is being operated upon. Flaps of skin are held back by hooks attached to rubber ties. The rubber ties are pulled taut once the hook has been engaged with the tissue and the ends of the rubber ties are then engaged with notches on an outer edge of the frame. This type of device is shown in FIG. 1.

During surgery on digits such as fingers, it is advantageous for the digit being operated upon to be held in an elevated orientation (relative to the hand) for a surgeon to operate. A difficulty with this is that when one digit is elevated, often the other digits will naturally tend to adopt an elevated orientation. Sometimes a digit which adopts a curled conformation must be straightened before it can be operated upon. During surgery, other digits (or the digit to be operated upon) are sometimes held down by lead weights, or by an assistant. These solutions can be unstable, inconvenient, crowded and/or labour intensive. It is amongst the objects of the present invention to solve one or more of these problems.

BRIEF SUMMARY OF THE INVENTION

In a first aspect the invention provides a frame for supporting a hand during surgery comprising;

- a plate having two wings which define a plane and a space therebetween, a support portion positioned between the two wings which comprises a supporting surface for two digits which is elevated relative to the plane defined by the wings. In some embodiments each wing is provided with an engaging feature for removably engaging a retaining tie.

The supporting surface provides an elevated surface for accommodating a digit. Two digits of a hand to be operated upon can be located and secured onto the supporting surface. This is useful in cases where either two digits need to be operated upon, or where there is such a strong tendency for a second digit to curl when a first digit to be operated upon is elevated, it is more convenient to elevate both digits. This provides a more versatile frame. The wings of the plate enable other digits of the hand to be held under the plate. This enables a surgeon to be presented with the digits in the correct elevated conformation, whilst the other digits of the hand are held out of the way, to provide access to the surgical area which, in use, may be positioned in the space created between the two wings. The position of the wings, the space therebetween, and the position of the supporting surface, provides a stable platform when engaged with a hand, at the same time as allowing two digits to be positioned correctly for surgery on the hand. An engaging feature on each wing may be provided so that a retaining tie can be engaged with the engaging feature. Retaining ties may comprise a hook at one end for engaging with a skin flap of a surgical area. The other end of the retaining tie may be engaged with the engaging feature so that the skin flap is retained in a retracted position. This enhances the access which a surgeon has to a surgical area in the space between the wings.

In some embodiments, the supporting surface is greater than 30 mm wide. In some embodiments it is between 30 and 100 mm wide, or between 30 and 60 mm wide, or between 60 and 100 mm wide. In some embodiments the supporting surface is between 30-100 mm long, and is more preferably 70-85 mm long. In some embodiments the supporting surface is generally rectangular when viewed in plan. In some embodiments the supporting surface is generally square when viewed in plan. In some embodiments the orientation of an axis of elongation of the supporting surface is generally perpendicular to a direction of extension of the wings. In some embodiments the supporting surface defines a ramp which is inclined with respect to the plane defined by the plate. The ramp assists in sliding a digit onto the frame as the hand is engaged with the frame. It also provides a stable surface onto which two digits may be secured.

In some embodiments the width of one or more of the wings is between 10-100 mm, more preferably between 20-60 mm and preferably 40 mm.

In some embodiments the engaging features comprise notches into which rubber tube of retaining ties may be jammed. In some embodiments the notches have a tapered entry portion and a slot portion into which a tube may be jammed.

In some embodiments the frame is formed from a single piece of material. In some embodiments the frame is formed from a metal or a polymer. The metal may be aluminium. In some embodiments the frame is formed from a MABS (methyl methacrylate acrylonitrile butadiene styrene) polymer, such as Terlux®. In some embodiments the frame is sterilizable.

In some embodiments the wings are tapered from a wide end, adjacent to the supporting surface, to a narrower end which is distal to the supporting surface. This provides enhanced rigidity of the frame whilst minimizing its size and material required for its manufacture.

In some embodiments the distance between an elevated end of the supporting surface and a distal end of the wings is between 100-200 mm.

In some embodiments the support portion is connected to the plate by sidewalls which are provided with an engaging feature for removably engaging a retaining tie. This provides a high degree of flexibility in engagement points for engaging retaining ties. This means that there is a lot of flexibility in the directions from which skin flaps may be restrained. These engaging features may also be used with securing devices according to the present invention to restrain a digit securely on the supporting surface. In some embodiments outer edges of the wings are provided without a lip or elevated flange.

In some embodiments the plate has an inner edge which defines the space between the two wings, the supporting surface defines a ramp which is inclined with respect to the plane defined by the plate and wherein the ramp extends to the inner edge of the plate. These features assist in sliding the digits to be operated upon onto the ramp. They also provide an ergonomic arrangement which minimizes strain on the digits being operated upon, and on the digits which are held under the plate in use.

In some embodiments the incline defined by the ramp is between 5 and 40 degrees. This assists with the engagement of digits with the supporting surface and also holds the digits in the correct elevated orientation for surgery.

In some embodiments the supporting surface is provided with a recess, concave shape or raised portions for accommodating two digits securely. This assists in preventing the digits from sliding off the supporting surface during surgery. In some embodiments the support portion is provided with two recesses or two concave shapes or raised portions for accommodating the two digits, or a combination thereof. These features may be orientated parallel to a length of the support surface. The raised portions may be ridges or raised sidewalls which run along the edges of the support surface, to stop digits from sliding off the support surface. In these, and other, embodiments the support surface may be flat/planar. This makes the frame suitable for a wider range of surgical procedures and more versatile in being able to work with a wider variety of patient's digits.

In some embodiments the support surface is provided with ridges, corrugations or grooves adapted to hold, secure or retain the finger on the support portion. These features may be orientated parallel to a length of the support surface.

In some embodiments the support portion has or comprises a W-shape, for example a W-shaped surface, a square topped/bottomed W-shaped surface, or a rounded topped/bottomed W-shaped surface. This provides a stable arrangement for accommodating two digits, which is also easy to manufacture, for example by injection moulding, for example in a one piece frame.

In some embodiments, an edge of the support portion is provided with two or three engaging features for removably engaging retaining ties. This provides flexibility and a useful number of points to which retaining ties can be attached to retain two of a patient's digits.

In some embodiments, an area of the support portion is greater than 30 $cm^2$. In some embodiments an area of the support portion is between 30 and 100 $cm^2$. In some embodiments an area of the support portion is between 35 and 60, 70, 80, 90 or 100 $cm^2$. This provides a surface which is large enough to stably accommodate two digits.

In some embodiments the plate has a horseshoe shape, an arrow shape or a triangular shape. The shape of the plate may in some embodiments be generally semi-circular, U-shaped or V-shaped. These shapes provide a base which is stable during surgery, with which a hand can be engaged.

In some embodiments the plate has an inner edge which defines the space between the two wings and outer edges which define outer portions of the two wings. In some embodiments the length of the inner edge is between 50-100 mm.

In some embodiments the space between the wings is generally U-shaped, V-shaped or has a semi-circular shape. The space may in some embodiments have generally horseshoe, arrow or triangular shape. These shapes provide preferred spaces to accommodate a surgical area in hand surgery, particularly in surgeries selected from Carpal tunnel release, Dupuytren's contracture fasciectomy, Trigger finger release, Tendon repair, Ganglion removal, Knuckle (MCP joint) replacement and Trapeziectomy (removal of the trapezium).

In some embodiments the engaging features are provided on outer edges of the two wings. This enables easy attachment of retainer ties to hold back skin flaps. Preferably a plurality of engaging features are provided on the outer edges of the wings. Preferably there are 2 or more, 5 or more, or 10 or more engaging features located on each wing.

In some embodiments the frame further comprises a retainer rib which protrudes from the plate, on the opposite side of the plate to the support portion. The retainer rib is useful for securely retaining digits which are located on the opposite side of the plate to the digit which is held on the support surface. The ribs may also provide rigidity to the plate which may assist the plate in resisting the forces involved in restraining digits in a desired conformation. In some embodiments the ribs enable a portion of the supporting surface to extend from adjacent to an inner edge of the plate from a level which is below the plane of the plate, with respect to the majority of the supporting surface (i.e. the majority of the supporting surface which is elevated from the plane of the plate). This allows the incline angle of the supporting surface relative to the plane of the plate to be lower than it would be if it did not extend from below the plate. This provides an ergonomic frame which reduces strain on digits during surgery.

In some embodiments the frame further comprises two retainer ribs which protrude from the plate, on the opposite side of the plate to the support portion, which retainer ribs are positioned on opposite sides of the support portion. This provides a stable frame when it is engaged with a hand.

In some embodiments the frame is formed from a single piece of material. This provides a rigid frame which is well adapted to deal with the forces involved in restraining digits during surgery. Preferably the frame is injection moulded.

In some embodiments the frame has a symmetry plane which is perpendicular to the plane defined by the wings. The symmetry plane provides a frame which is stable when engaged with a hand. In some embodiments the symmetry plane passes through the support surface. This provides a frame which is stable when engaged with a hand.

In another aspect of the invention there is provided a securing device for securing two digits on a frame during surgery comprising;

- a rigid body with a contacting surface for contacting a digit which is supported on a frame,
- elongate retaining ties extending from opposite sides of the rigid body,
- wherein the elongate retaining ties are stretchable in a longitudinal direction.

In some embodiments, the contacting surface has a length of at least 3 cm or at least 4, 5 or 6 cm.

The length of the contacting surface is useful for accommodating two fingers so that two of a patient's fingers can be held down onto a frame using a single securing device. This makes it easier, faster to prepare a hand for surgery. It also provides a hand which is more stably restrained and provides more options for restraining a hand during surgery.

In some embodiments the contacting surface has an area of greater than 5 $cm^2$, or greater than 6, 8, 10, 16 or 25 $cm^2$. This provides an area which can stably engage two digits.

In some embodiments the body comprises two apertures in the plane of the body, through which an elongate tie member passes to form the elongate retaining ties. This provides a body which is easy to manufacture and assemble and is robust.

In some embodiments the securing device comprises a groove for accommodating the elongate tie member, which is on an opposite face of the body to the contact surface and which is between the two apertures. This provides a less bulky securing device, which is still easy to manufacture and can be adjusted easily.

In use, the rigid body may be positioned on the tips of two fingers which are located on a supporting surface of a frame according to the invention. The contacting surface stably engages with the digits. The elongate retaining ties may then be engaged with engaging features of a frame to retain the tips of the digits in a desired position. The longitudinal stretch in the elongate retaining ties is useful because they may be engaged with engaging features whilst they are in a stretched conformation. The strain in the stretched ties therefore retains the tips of the fingers securely. In some embodiments the stretching ability of the elongate retaining ties is low. That is the elongate retaining ties may be highly resilient to allow high levels of force to be applied to digits to restrain them.

In some embodiments the elongate retaining ties comprise, or are formed of, a polymer tube. In some embodiments the elongate retaining ties are formed from a single piece of material. In some embodiments the contacting surface is concave, so as to provide a stable engagement with the tips of two fingers.

In some embodiments the contacting surface comprises a non-slip portion, which may cover the whole of the contacting surface. In some embodiments the contacting surface is non-slip to provide a secure engagement with the tips of two digits.

In some embodiments the elongate retaining ties are resiliently compressible in a radial direction. This assists with their engagement with an engaging feature such as a notch because the resilience allows them to be jammed into a notch.

In some embodiments, the rigid body is provided with an aperture through which a single piece of material is threaded to form the elongate retaining ties. The piece of material may be threaded to retain it in position in relation to the rigid body.

In some embodiments the elongate retaining ties have free ends having a length of at least 90 mm. Preferably the rigid body has an oval shape.

In some embodiments the elongate retaining ties comprise, or consist of a polymer. Preferably the elongate retaining ties are tubular. They preferably have a diameter of between 1 mm and 5 mm.

In a further aspect of the invention there is provided a kit comprising a frame as described herein and a securing device as described herein.

In some embodiments the kit comprises two securing devices as described herein. In some embodiments the kit comprises one or more, and preferably 4, retaining ties as described herein. In some embodiments the kit comprises one or more, and preferably 4 non-hooked retaining ties. These may be engaged with the engaging features of the frame to restrain digits, or the hand as a whole, in a desired conformation (without holding back any skin flaps).

In a further aspect of the invention there is provided a method of preparing a hand for surgery comprising the steps of;

providing a frame as described herein and
engaging a hand with the frame.

In some embodiments the surgery for which the hand is prepared is selected from a surgery of the fingers and/or wrist, nerves or vasculature. The surgery for which the hand is prepared may be selected from Carpal tunnel release, Dupuytren's contracture fasciectomy, Trigger finger release, Tendon repair, Ganglion removal, Knuckle (MCP joint) replacement and Trapeziectomy (removal of the trapezium).

In some embodiments the step of engaging the hand with the frame comprises the step of inserting two digits of the hand through the space between the wings of the frame such that, the digits are supported on the supporting surface, and
another digit of the hand remains on the opposite side of the plane defined by the plate to the supporting surface.

In some embodiments the method further comprises the step of securing the two digits on the supporting surface by engaging the elongate retaining ties of a securing device as described herein to engaging features of the frame such that the contacting surface of the securing device contacts the digits which are supported on the supporting surface of the frame.

In a further aspect the invention provides a method of surgery which comprises a method of preparing a hand for surgery as described herein, followed by a surgical procedure. In some embodiments the surgical procedure may be selected from a surgery of the fingers and/or wrist, nerves or vasculature. The surgical procedure may be selected from Carpal tunnel release, Dupuytren's contracture fasciectomy, Trigger finger release, Tendon repair, Ganglion removal, Knuckle (MCP joint) replacement and Trapeziectomy (removal of the trapezium).

BRIEF DESCRIPTION OF THE DRAWINGS

An embodiment of the invention will now be described with reference to the figures of the drawings, in which.

DETAILED DESCRIPTION OF THE INVENTION

FIGS. 2-9 show frames and securing devices which fall outside the scope of the invention. However their features are useful for understanding the invention and further embodiments of the invention may combine any of the features shown in FIGS. 1-9 with the features shown in FIGS. 10-14 and/or those features disclosed in the statements of invention above.

Figure 1:
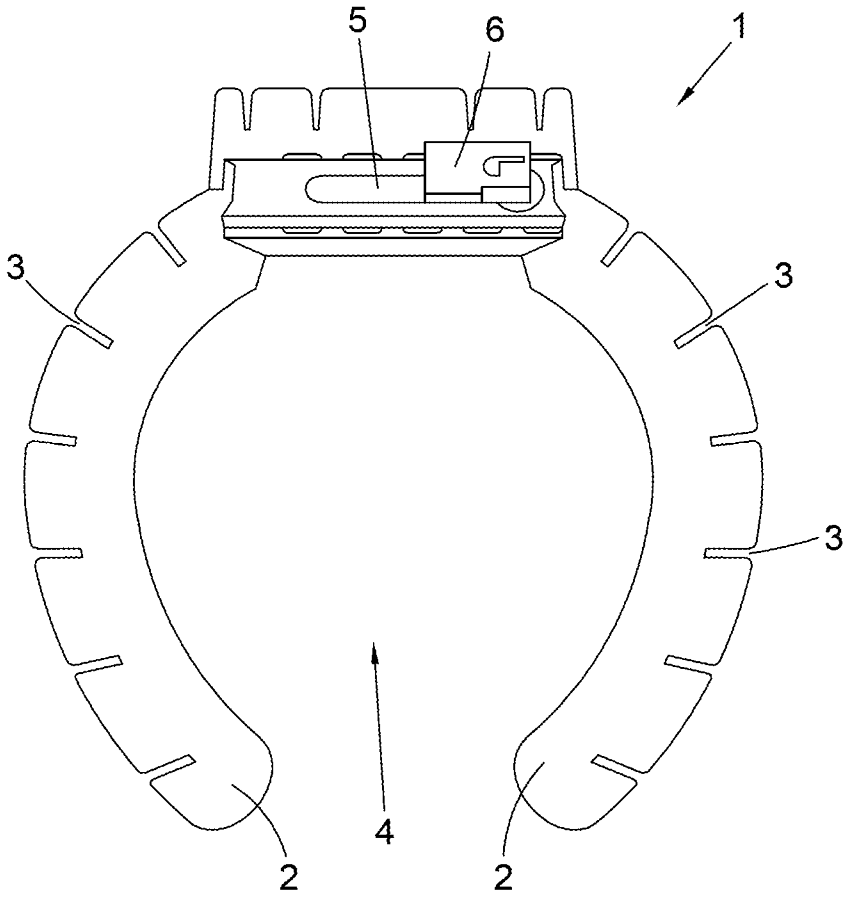
FIG. 1 PRIOR ART
FIG. 1 shows a retractor frame according to the prior art.

FIG. 1 shows a frame 1 which has two narrow arms 2. The arms 2 are provided with notches 3 around their outer edges and are curved. The retractor frame is positioned such that tissue to be operated upon is located below the space 4 between the arms. An incision is made in the tissue and the edges of the incision are engaged by hooks attached to ties (not shown). The ties are tautened to apply tension to the edges of the incision and then engaged with the notches 3. Between the two arms, there is an adjustable track 5 and cam lock fastener 6. The track and fastener allow a surgeon to adjust the relative distance between the two arms, to provide a greater space between the arms. The frame can therefore be adjusted to be used in operations on tissue areas of different sizes.

Figure 2:
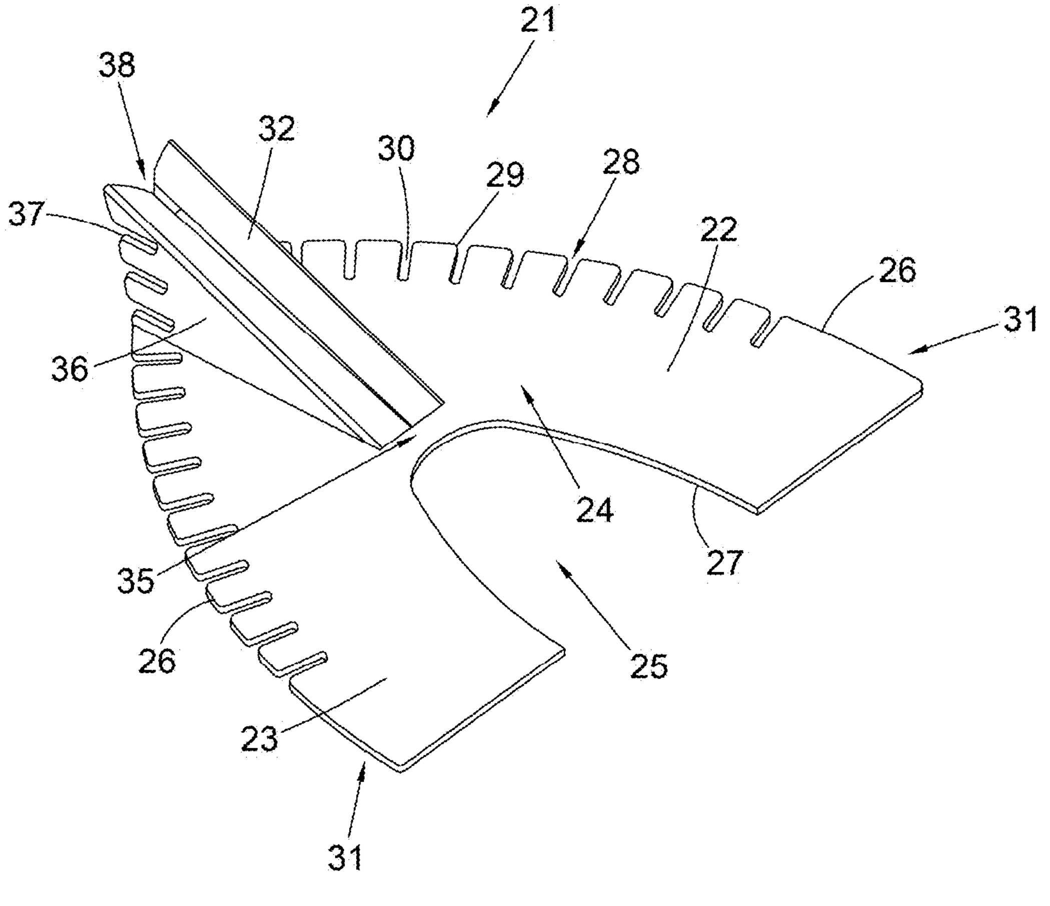
FIG. 2 shows a perspective view of a frame according to a reference example.
Figure 3:
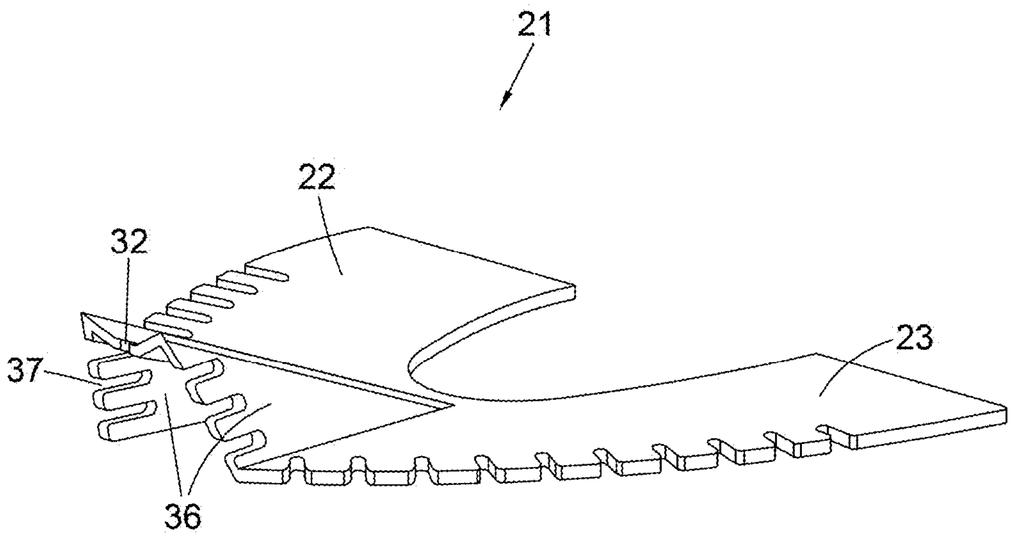
FIG. 3 shows a second perspective view of the frame of FIG. 2.
Figure 4:
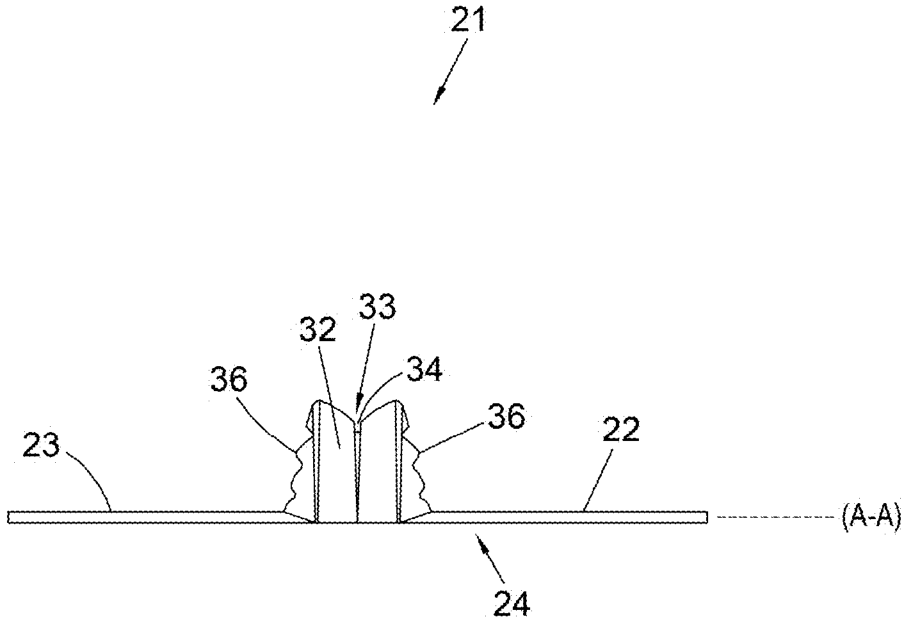
FIG. 4 shows a front view of the frame of FIG. 2.
Figure 5:
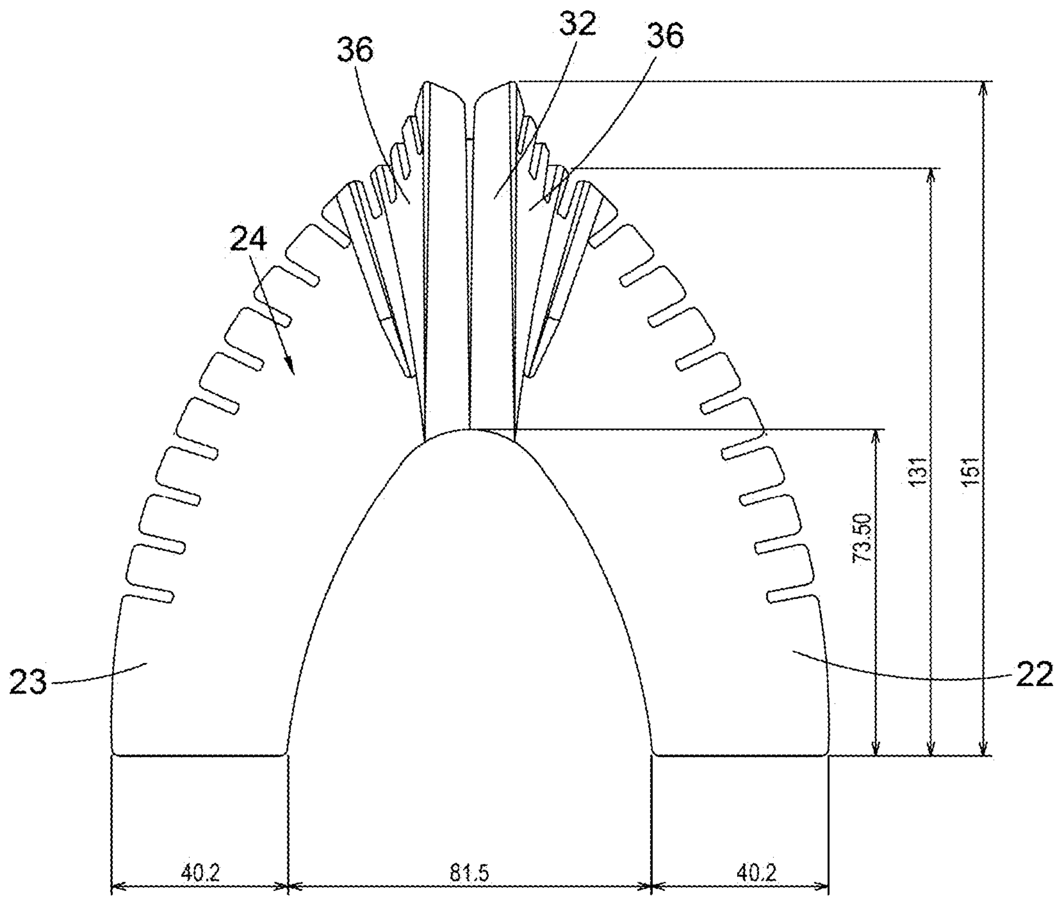
FIG. 5 shows a plan view of a frame according to a second reference.
Figure 6:
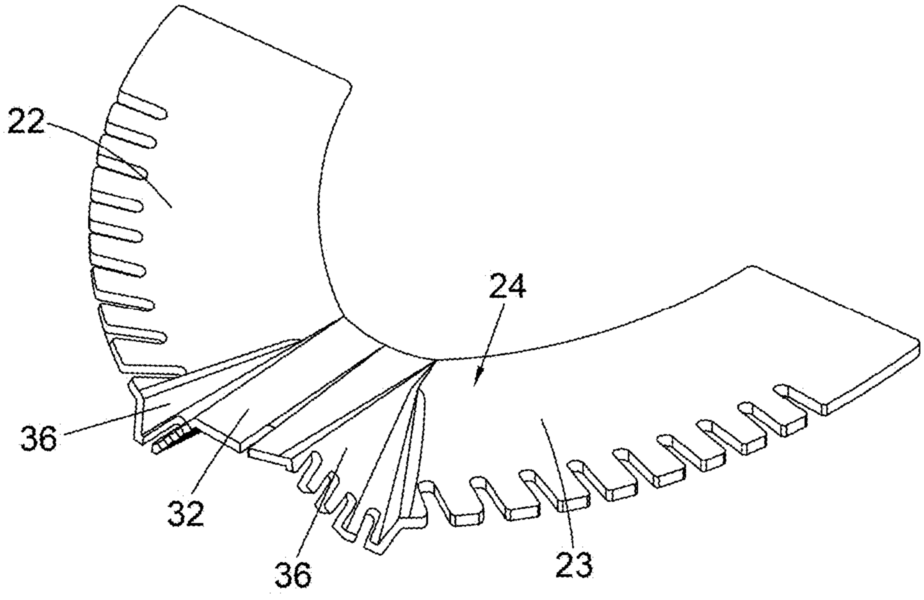
FIG. 6 shows a perspective view of the frame of FIG. 5.
Figure 7:
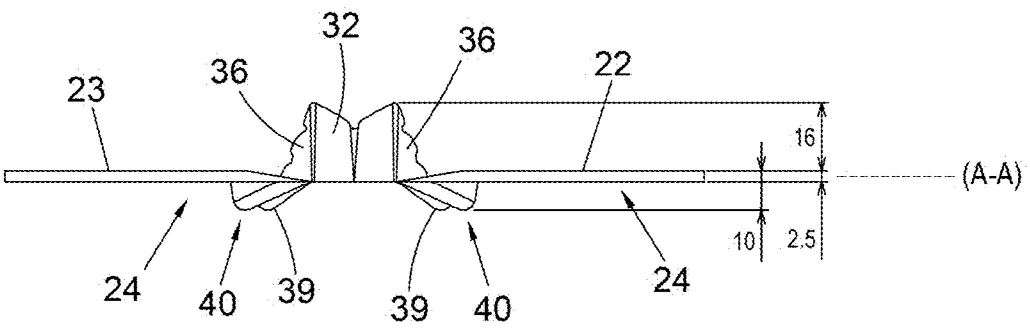
FIG. 7 shows a front view of the frame of FIG. 5.

FIGS. 2-4 show a frame 21. The frame is made from Terlux® which is a methyl methacrylate acrylonitrile butadiene styrene (MABS) polymer. The polymer is suitable for injection moulding and in this embodiment the frame is injection moulded. Terlux® is obtainable from Ineos Capital Limited, of 38 Hans Crescent Knightsbridge, London, UK.

The frame has a planar plate 24 formed with two wings 22, 23 which define a space 25 therebetween. The plate 24 has a generally U-shaped configuration, having an outer edge 26 and an inner edge 27. The frame is formed from a plastics material. The inner edge 27 has a U-shape, to define the elongated semicircular space 25 between the wings 23 and 22. The outer edge 26 of each wing is provided with a series of notches 28 which are regularly spaced apart along the outer edge. Each notch comprises a flared entry portion 29 and a narrower slot portion 30. An end portion 31 of the outer edge of each wing is left free of notches. This provides a tab by which a surgeon can easily hold the frame to position it properly.

Between the two wings, the frame has a raised support surface 32. The support surface is a ramp which extends from close to the inner edge 27 of the plate 24. However, there is a space 35 between the ramp and the inner edge of the plate. The ramp is rectangular when viewed in plan. It has a V shaped profile 33 which is formed by a fold 34 down the centre of the ramp. The ramp is inclined at an angle of 25 degrees to the plane (A-A) which is defined by the plate 24. The support surface is connected to the wings 22 and 23 of the frame by sidewalls 36. The sidewalls 36 are formed from the same piece of material which forms the wings 22 and 23. The sidewalls have edges which run into the outer edges 26 of the wings. The edges of the sidewalls are also provided with notches 37 which in this embodiment are identical to the notches 28 on the outer edges of the wings. The upper end of the supporting surface is also provided with a notch 38 which is adapted to engage a retaining tie in the same way that notches 28 are adapted to engage a retaining tie.

FIGS. 5-8 show a frame according to a second reference example. The frame is made from Terlux®. Features which are similar to the features of the first embodiment are provided with corresponding reference numerals. The sidewalls 36 which connect the support surface 32 to the wings 23 and 22 are different to the sidewalls shown in the first embodiment. The sidewalls 36 extend from the support surface 32 towards the plane (A-A) which is defined by the plate 24. They pass through the plane A-A and extend to the opposite side of the plane to the support surface 32. On that opposite side of the plane the sidewalls 36 meet rib walls 39 which form ribs which protrude from the plane A-A of the plate 24. The rib walls 39 define ribs 40 which extend along either side of the support surface, only on the opposite side of the plane A-A to the support surface. The exemplary (non-limiting) measurements shown on this embodiment are in mm, but other measurements may also be used.

Figure 8:
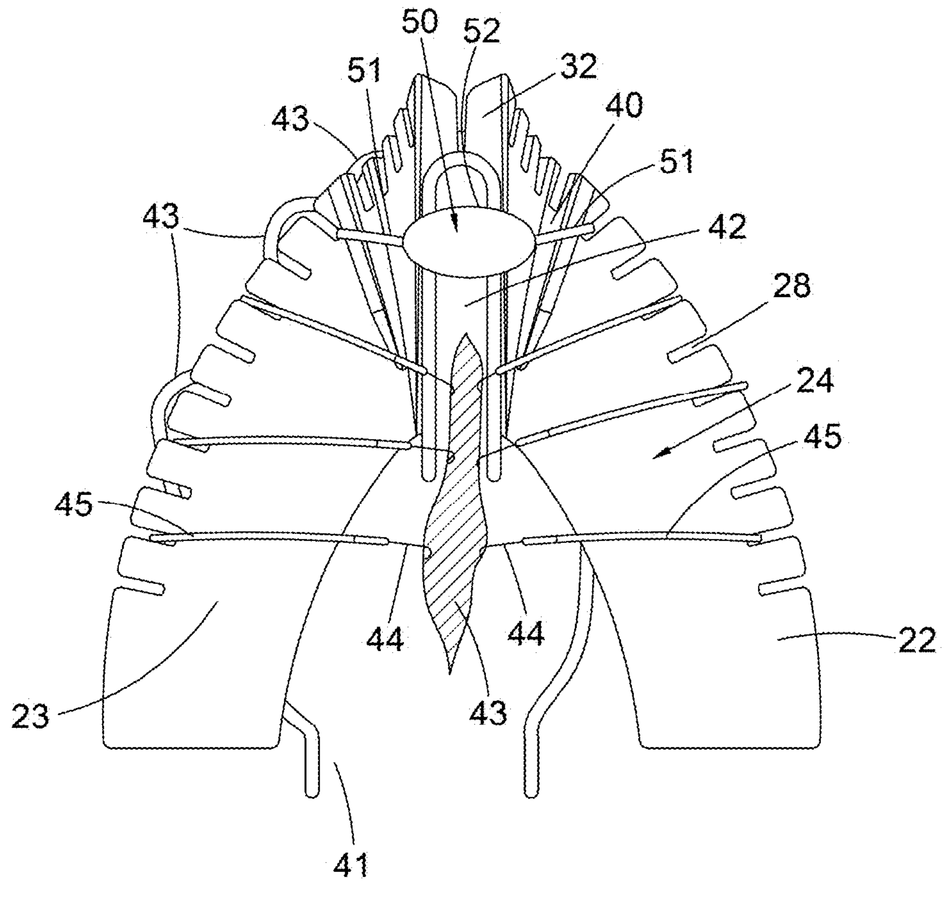
FIG. 8 shows a plan schematic view of the frame of FIGS. 5-7 in use in conjunction with a securing device.

FIG. 8 shows a hand 41 engaged with the frame 21 during surgery. A single digit 42 is being operated upon. The hand is engaged with the frame such that the single digit 42 is resting upon the support surface 32. The remaining fingers 43 and thumb (not shown) of the hand are located below the wings 22 and 23 of the plate 24. The surgeon's incision 43 is shown in the space between the wings 22 and 23. The edges of the incision are engaged with hooks 44, which are attached to retaining ties 45. The ends of the retaining ties 45 are engaged with notches 28 on the outer edge of the wings 22 and 23, such that the edges of the incision are held back to provide the surgeon with access to the underlying tissue. The ribs 40 which protrude from the opposite side of the plate 24 to the supporting surface 32 prevent the digits 43 from moving behind the digit 42 or shifting in that direction, and thereby hold the hand securely in place relative to the frame. A securing device 50 is engaged with the tip of the finger 42 which is being operated upon. This secures the finger 42 in an elevated conformation on the supporting surface 32. The securing device comprises two stretchable polymer ties 51 which are attached to a central rigid body 52. The rigid body is formed from a curved piece of plastic which is adapted to conform to the curvature of the tip of the finger 42. The elongate ties are radially compressible so that they may be fed through the notches 28 and engaged/jammed in the notches 28. The stretchable nature of the ties allows pressure to be exerted on the tip of the finger to stop it from curling upwardly during surgery, or falling off the supporting surface 32.

Figure 9A:
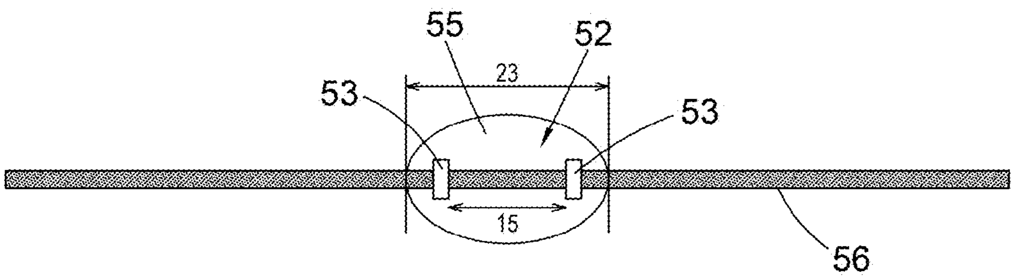
FIGS. 9A and 9B are plan and side views respectively of a reference example of a securing device.
Figure 9B:
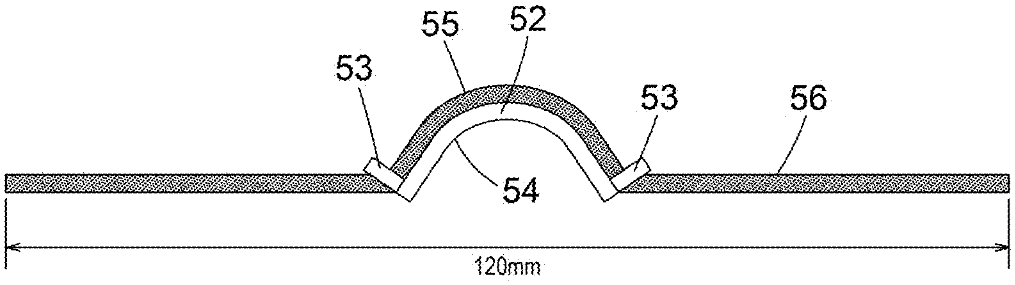

A reference example of a securing device is shown in FIGS. 9A and 9B. FIG. 9A shows a plan view of the securing device. FIG. 9B shows a side view of the securing device. The securing device has a rigid plastic body portion 52 which is generally oval in a plan view. The body portion is curved to provide a concave bottom face 54 which conforms with the shape of the tip of a digit such as a finger. A top, convex face 55 of the body portion is provided with two loops 53. A stretchy polymer tube 56 is threaded through these loops such that the free ends of the tube extend from the loops. These free ends of the tube may be engaged with engaging features such as notches on a frame. The tube is radially compressible to aid this engagement. The position of the body portion on the tube can be adjusted by sliding the body portion along the tube. This allows one end of the tube to be engaged, the body to be moved into the correct position to engage a digit, and the other end of the tube to be engaged with a second engaging portion. The dimensions shown on the figure are in mm, although other dimensions can be used.

Figure 10:
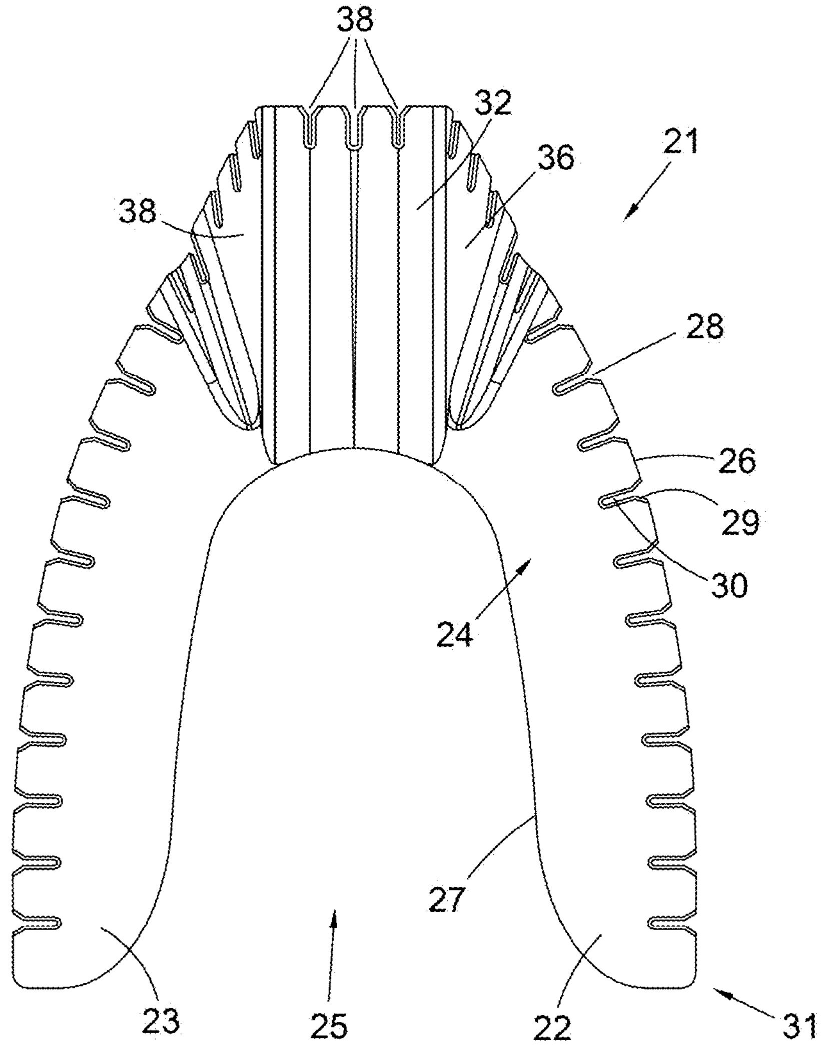
FIGS. 10-12 show a frame according to the invention.
Figure 11:
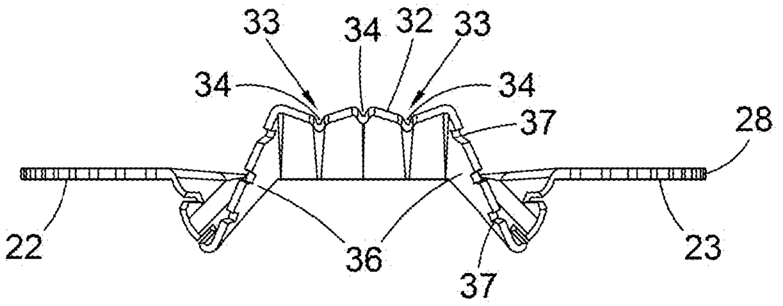
Figure 12:
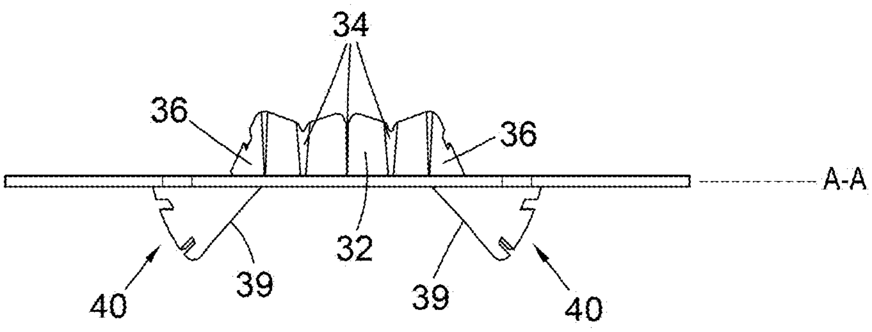

FIGS. 10-12 show a frame according to the invention. Features which correspond to the features of the reference examples shown in FIGS. 1-9 are shown using corresponding reference numerals.

FIGS. 10-12 show a frame 21. FIG. 10 is a plan view of the frame. FIG. 11 is a front view of the frame. FIG. 12 is a rear view of the frame. The frame is made from Terlux® which is a methyl methacrylate acrylonitrile butadiene styrene (MABS) polymer. The polymer is suitable for injection moulding and in this embodiment the frame is injection moulded. Terlux® is obtainable from Ineos Capital Limited, of 38 Hans Crescent Knightsbridge, London, UK.

The frame has a planar plate 24 formed with two wings 22, 23 which define a space 25 therebetween. The plate 24 has a generally U-shaped configuration, having an outer edge 26 and an inner edge 27. The frame is formed from a plastics material. The inner edge 27 has a U-shape, to define the elongated semicircular space 25 between the wings 23 and 22. The outer edge 26 of each wing is provided with a series of notches 28 which are regularly spaced apart along the outer edge. Each notch comprises a flared entry portion 29 and a narrower slot portion 30. An end portion 31 of the outer edge of each wing is left free of notches. This provides a tab by which a surgeon can easily hold the frame to position it properly.

Between the two wings, the frame has a raised support surface 32. The support surface is a ramp which extends from the inner edge 27 of the plate 24. The support portion is 4 cm wide, but other widths greater than 3 cm may be used. The support portion has an area of 40 $cm^2$ however in other embodiments areas of greater than 30 $cm^2$ may be used. The ramp is a compressed rectangle when viewed in plan. In other embodiments the support portion may be generally square when viewed from above. It has a W-shaped profile 33 which is formed by three folds 34 down the ramp. The folds provide two troughs/recesses, each of which is adapted to provide a stable base for a digit resting on the support surface. In other embodiments raised portions such as ridges may be provided along the outer edges of the support portion and optionally along a centre of the support portion, running along the length of the support portion, to keep digits separate, and retained on the support portion. The ramp is inclined at an angle of 25 degrees to the plane (A-A) which is defined by the plate 24. The support surface is connected to the wings 22 and 23 of the frame by sidewalls 36. The sidewalls 36 are formed from the same piece of material which forms the wings 22 and 23. The sidewalls have edges which run into the outer edges 26 of the wings. The edges of the sidewalls are also provided with notches 37 which in this embodiment are identical to the notches 28 on the outer edges of the wings. The upper end of the supporting surface is also provided with three notches 38 which are adapted to engage a retaining tie in the same way that notches 28 are adapted to engage a retaining tie. In other embodiments the supporting surface may be provided with two notches 38.

The sidewalls 36 extend from the support surface 32 towards the plane (A-A) which is defined by the plate 24. They pass through the plane A-A and extend to the opposite side of the plane to the support surface 32. On that opposite side of the plane the sidewalls 36 meet rib walls 39 which form ribs which protrude from the plane A-A of the plate 24. The rib walls 39 define ribs 40 which extend along either side of the support surface, only on the opposite side of the plane A-A to the support surface.

Figure 13:
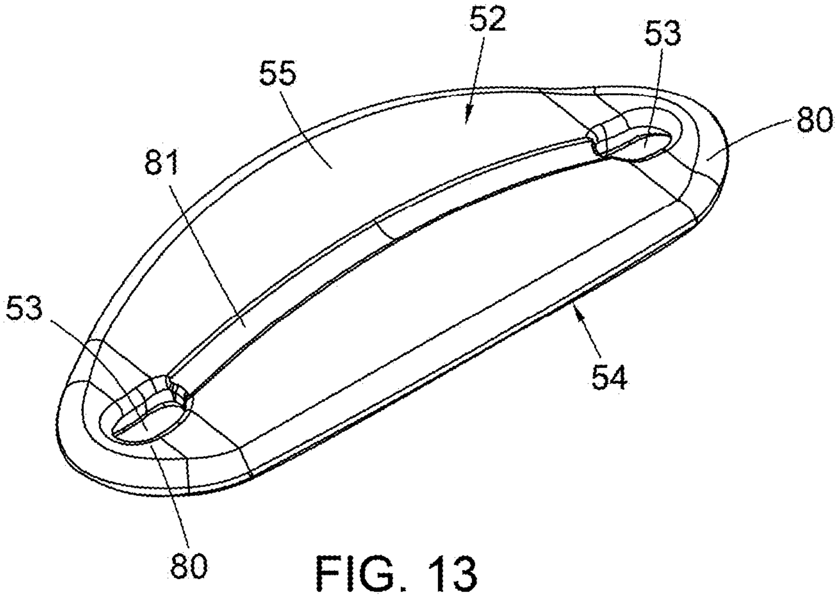
FIGS. 13 and 14 show a securing device according to the invention.
Figure 14:
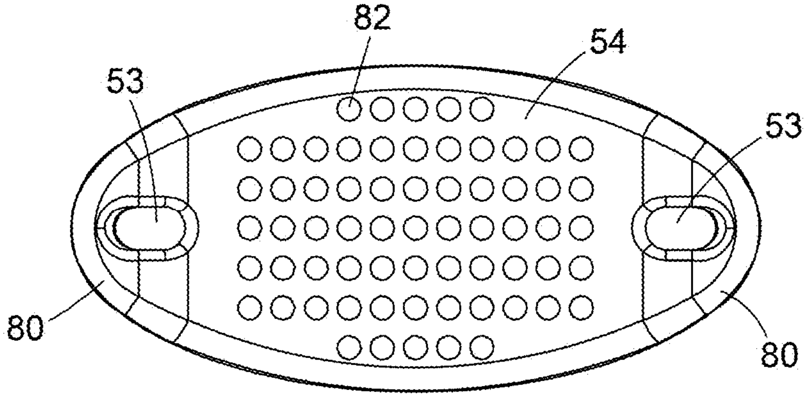

FIGS. 13 and 14 show a body of a securing device according to the invention. The securing device utilizes the retaining tie shown in FIGS. 9A and 9B, or similar.

FIG. 13 shows a top perspective view of the body of securing device. FIG. 14 shows a bottom perspective view of the body of the securing device. The securing device has a rigid plastic body portion 52 which is generally oval in a plan view. The body portion is curved to provide a concave bottom face 54 which conforms with the shape of the tips of two digits such as fingers. The length of the portion of the bottom face 54 which is adapted to contact digits secured to a frame is 4 cm. The area of the portion of the bottom face 54 which is adapted to contact digits secured to a frame is 8 $cm^2$.

A top, convex face 55 of the body portion body portion is provided with two apertures 53 which are formed in the plane of the body 52. No features protrude from the upper surface 55 of the body 52. The interior corners of the apertures are rounded. The apertures are both spaced by the same distance from the a respective end of the body. The apertures are located is tabs 80 at each end of the body which adopt a planar, flat orientation with respect to the concave/convex surfaces 55 and 54 of the body. A stretchy polymer tube is threaded through these apertures 53, in a similar manner to the arrangement shown in FIGS. 9A and 9B, such that the free ends of the tube extend from the underside of the apertures 53.

That is, the polymer tube exits the apertures adjacent to bottom face 54. The portion of the polymer tube which is between the apertures 53 sits in a groove 81 (shown in FIG. 13) in the convex face 55 of the body. The groove 81 has a U-shaped cross section. The free ends of the tube may be engaged with engaging features such as notches on a frame. The tube is radially compressible to aid this engagement. The position of the body portion on the tube can be adjusted by sliding the body portion 52 along the tube. This allows one end of the tube to be engaged, the body to be moved into the correct position to engage a digit, and the other end of the tube to be engaged with a second engaging portion. The concave face 54 is provided with an array of gripping 82 features. These gripping features may be protrusions, or areas of a non-slip material.

The invention claimed is:

1. A method of preparing a hand for surgery comprising the steps of:

providing a frame for supporting a hand during surgery, the frame comprising a plate having two wings which define a plane and a space therebetween, and a support portion positioned between the two wings which comprises a supporting surface for two digits which is elevated relative to the plane defined by the wings, wherein each wing is provided with an engaging feature for removably engaging a retaining tie; and engaging a hand with the frame, wherein the step of engaging the hand with the frame comprises the step of inserting two digits of the hand through the space between the wings of the frame such that the digits are supported on the supporting surface, and another digit of the hand remains on the opposite side of the plane defined by the plate to the supporting surface.

2. The method according to claim 1, wherein the support portion is provided with two recesses or two concave shapes or raised portions for accommodating the two digits.

3. The method according to claim 1, wherein the support portion is substantially square when viewed from above or below.

4. The method according to claim 1, wherein the support portion has a width of greater than 30 mm.

5. The method according to claim 1, wherein the support portion has a width of between 30 mm and 60 mm.

6. The method according to claim 1, wherein the support portion has a W-shaped surface.

7. The method according to claim 1, wherein an edge of the support portion is provided with three engaging features for removably engaging retaining ties.

8. The method according to claim 1, wherein an area of the support portion is greater than 30 $cm^2$.

9. The method according to claim 1, wherein the supporting surface defines a ramp which is inclined with respect to the plane defined by the plate.

10. The method according to claim 1, wherein the space between the wings is substantially U-shaped, V-shaped or has a semi-circular shape.

11. The method according to claim 1, the frame further comprising:

two retainer ribs which protrude from the plate on an opposite side of the plate to the support portion, wherein the retainer ribs are positioned on opposite sides of the support portion.

12. The method according to claim 1, wherein the frame is formed from a single piece of material.

13. The method according to claim 1, wherein the providing the frame comprises providing a kit comprising the frame, the kit further comprising a securing device for securing two digits on the frame during surgery, wherein the securing device comprises:

a rigid body with a contacting surface for contacting a digit which is supported on a frame; and elongate retaining ties extending from opposite sides of the rigid body, wherein the elongate retaining ties are stretchable in a longitudinal direction, and wherein the contacting surface has a length of at least 3 cm.

14. The method according to claim 1, further comprising the step of securing the two digits on the supporting surface by engaging the elongate retaining ties of a securing device to engaging features of the frame such that the contacting surface of the securing device contacts the two digits which are supported on the supporting surface of the frame, wherein the securing device comprises:

a rigid body with a contacting surface for contacting a digit which is supported on a frame; and elongate retaining ties extending from opposite sides of the rigid body, wherein the elongate retaining ties are stretchable in a longitudinal direction, and wherein the contacting surface has a length of at least 3 cm.

15. The method according to claim 1, further comprising securing at least one of the two digits to the supporting surface by engaging at least one retaining tie with the engaging feature of one or both wings.

16. The method according to claim 15, wherein securing the two digits comprises engaging elongate retaining ties of a securing device with the engaging features of the frame such that a contacting surface of the securing device presses the two digits against the supporting surface.

17. The method according to claim 16, wherein securing the two digits comprises stretching the elongate retaining ties and retaining them in a stretched condition to apply a downward force to the digits.

18. The method according to claim 1, further comprising performing a surgical procedure on at least one of the two digits while the hand is engaged with the frame.

19. The method according to claim 18, wherein the surgical procedure is selected from the group consisting of carpal tunnel release, Dupuytren's contracture fasciectomy, trigger finger release, tendon repair, ganglion removal, knuckle replacement, and trapeziectomy.

20. The method according to claim 18, wherein performing the surgical procedure comprises making an incision in tissue positioned within the space between the wings of the frame.

* * * * *